United States Patent
Shi et al.

(10) Patent No.: US 10,071,119 B2
(45) Date of Patent: Sep. 11, 2018

(54) APPLICATION OF MESENCHYMAL STEM CELLS IN PROPHYLAXIS OR TREATMENT OF STRESS RESPONSE-INDUCED WEAKENED IMMUNITY

(71) Applicant: Shanghai Institute For Biological Sciences, Chinese Academy Of Sciences, Shanghai (CN)

(72) Inventors: Yufang Shi, Shanghai (CN); Gang Cao, Shanghai (CN)

(73) Assignee: Shanghai Institutes For Biological Sciences, Chinese Academy Of Sciences, Shanghai (CN)

( * ) Notice: Subject to any disclaimer, the term of this patent is extended or adjusted under 35 U.S.C. 154(b) by 43 days.

(21) Appl. No.: 14/889,981

(22) PCT Filed: Apr. 29, 2014

(86) PCT No.: PCT/CN2014/076511
§ 371 (c)(1),
(2) Date: Nov. 9, 2015

(87) PCT Pub. No.: WO2014/180269
PCT Pub. Date: Nov. 13, 2014

(65) Prior Publication Data
US 2016/0120908 A1 May 5, 2016

(30) Foreign Application Priority Data
May 8, 2013 (CN) .......................... 2013 1 0170161

(51) Int. Cl.
*A61K 35/28* (2015.01)
*A61K 38/20* (2006.01)
*G01N 33/50* (2006.01)

(52) U.S. Cl.
CPC .......... *A61K 35/28* (2013.01); *A61K 38/2026* (2013.01); *G01N 33/5023* (2013.01); *G01N 33/5047* (2013.01); *G01N 2333/5406* (2013.01); *G01N 2333/7051* (2013.01); *G01N 2333/70596* (2013.01)

(58) Field of Classification Search
CPC ............................ A61K 35/28; A61K 38/2026
See application file for complete search history.

(56) References Cited

U.S. PATENT DOCUMENTS

2005/0239897 A1* 10/2005 Pittenger ................ A61K 35/28
514/569
2009/0202479 A1 8/2009 Shi et al.

FOREIGN PATENT DOCUMENTS

| AU | 2012258424 A1 | 12/2012 |
|---|---|---|
| CN | 101384702 A | 3/2009 |
| CN | 102719397 A | 10/2012 |

OTHER PUBLICATIONS

Lemaire et al. Cell Death Differ. Aug. 1999;6(8):813-820.*
Brunetti et al., Blood. Dec. 1, 1995;86(11):4199-4205.*
Lee et al., Int Immunopharmacol. Jun. 2012;13(2):219-224.*
Xiao et al., Transfusion. Dec. 2012;52(12):2551-2558.*
Zhang et al., J.Neuroimmunology (1998) 92:139-151.*
Wang et al., Clinical applications of mesenchymal stem cells. J Hematol Oncol. Apr. 30, 2012;5:19. doi: 10.1186/1756-8722-5-19.
Wang et al., Effects of Mesenchymal Stem Cells on Thymus Tissue Injury Induced by Ionizing Radiation in Mice. J Jilin University (Med Ed.). Mar. 31, 2009;35:265.
Cao et al., Mesenchymal stem cells prevent restraint stress-induced lymphocyte depletion via interleukin-4. Brain Behav Immun. May 2014:38:125-32. doi: 10.1016/j.bbi.2014.01.013. Epub Jan. 27, 2014.
Fan et al., Preliminary studies on Transplantation of umbilical cord mesenchymal stem cell to treat liver cirrhosis. Soochow University. 2010.
Li et al., Mesenchymal stem cells: a double-edged sword in regulating immune responses. Cell Death Differ. Sep. 2012;19(9):1505-13. doi: 10.1038/cdd.2012.26. Epub Mar. 16, 2012.
Najar et al., Mesenchymal stromal cells promote or suppress the proliferation of T lymphocytes from cord blood and peripheral blood: the importance of low cell ratio and role of interleukin-6. Cytotherapy. 2009:11(5):570-83. doi: 10.1080/14653240903079377.
Tomchuck et al., Mesenchymal stem cells as a novel vaccine platform. Front Cell Infect Microbiol. Nov. 16, 2012;2:140. doi: 10.3389/fcimb.2012.00140. eCollection 2012.

* cited by examiner

Primary Examiner — Daniel C Gamett
(74) Attorney, Agent, or Firm — Wolf, Greenfield & Sacks, P.C.

(57) ABSTRACT

The present invention discloses the application of mesenchymal stem cells in the prophylaxis or treatment of stress response-induced weakened immunity. More particularly, the present invention provides the use of mesenchymal stem cells in preparing a pharmaceutical composition for the prophylaxis or treatment of stress response-induced lymphopenia; and/or the use thereof in preparing a pharmaceutical composition for the prophylaxis or treatment of stress response-induced weakened immunity; and/or the use thereof in preparing a pharmaceutical composition for the promotion of interleukin 4 (IL-4) expression and/or enhanced or strengthened activity. The present invention has found that mesenchymal stem cells can, by means of regulating IL-4 and down-stream related signaling pathways, protect against hormonal disorder-induced lymphopenia, thus having the function of activating immune response.

9 Claims, 7 Drawing Sheets

APPLICATION OF MESENCHYMAL STEM CELLS IN PROPHYLAXIS OR TREATMENT OF STRESS RESPONSE-INDUCED WEAKENED IMMUNITY

RELATED APPLICATIONS

This application is a national stage filing under 35 U.S.C. § 371 of International Application PCT/CN2014/076511 entitled "APPLICATION OF MESENCHYMAL STEM CELLS IN PROPHYLAXIS OR TREATMENT OF STRESS RESPONSE-INDUCED WEAKENED IMMUNITY" filed Apr. 29, 2014, which claims priority to CN Application No. 201310170161.0, filed May 8, 2013, the entire disclosure of each of which is incorporated by reference in its entirety.

TECHNICAL FIELD

The present disclosure relates to the field of bio-medicine. Particularly, the present disclosure discloses the use of mesenchymal stem cells for preventing or treating lymphocyte reduction and/or immunosuppression induced by stress responses.

BACKGROUND

In the past few decades, epidemiological evidences and conventional life experiences have suggested that physiological stress will severely damage human health. On one hand, stress will directly promote development and progression of diseases. For example, it was demonstrated through researches that the p53 (a cancer suppressor gene) protein levels in mice can be down-regulated by glucocorticoids secreted during stress state, thereby contributing to tumorigenesis. On the other hand, more and more attention has been paid to the indirect effects of stress on promoting development and progression of diseases, particularly to its down-regulating effect on immune system.

The decrease of the immune function plays a critical role in the development and progression of many diseases. The down-regulated immune function can easily allow the onset of virus infection, delayed wound healing and increased risk of cancer rate, etc.

Although there are great progresses in the understanding of the contribution of stress to the pathogenesis and progression of diseases, however, effective countermeasures against stress still await development. There is a need for the clinic to develop effective measures to relieve the negative influence of stress on the development and progression of diseases.

Therefore, there is an urgent need in the art to develop a medicament for fighting against the negative influence of stress and improving immune function as well.

SUMMARY OF THE DISCLOSURE

A method of using mesenchymal stem cells for fighting against immune system diseases induced by excessive stress responses is provided by the disclosure.

In the first aspect of the present disclosure, a use of mesenchymal stem cells is provided for preparing a pharmaceutical composition to prevent or treat stress response-induced lymphocyte reduction and/or stress response-induced immunosuppression.

In another preferred embodiment, said stress response-induced lymphocyte reduction comprises the lymphocyte reduction induced by increased glucocorticoids.

In another preferred embodiment, the lymphocytes comprise T-lymphocytes or B-lymphocytes.

In another preferred embodiment, said lymphocyte reduction comprises the lymphocyte reduction induced by apoptosis.

In another preferred embodiment, said immunosuppression includes lymphocyte reduction, or decrease in the expression and/or activity of Interleukin-4 (IL-4).

In another preferred embodiment, said mesenchymal stem cells comprise umbilical cord mesenchymal stem cells, adipose mesenchymal stem cells, bone marrow mesenchymal stem cells, placenta mesenchymal stem cells, or amniotic fluid mesenchymal stem cells.

In another preferred embodiment, said mesenchymal stem cells are derived from mammals, preferably, from human, mouse, or rat.

In another preferred embodiment, said pharmaceutical composition comprises mesenchymal stem cells and pharmaceutically acceptable carriers.

In anther preferred embodiment, said pharmaceutical composition is in a liquid form and comprises $0.05\text{-}10 \times 10^6$ cells/ml, preferably, $0.05\text{-}5) < 10^6$ cells/ml, more preferably, $0.5\text{-}2 \times 10^6$ cells/ml.

In another preferred embodiment, the application dosage of said mesenchymal stem cells is $0.01\text{-}100) < 10^6$ mesenchymal stem cells/kg.

In another preferred embodiment, said pharmaceutical composition further comprises additional active ingredient IL-4.

In another preferred embodiment, the pharmaceutical composition can further activate IL-4 signal pathway molecules, IL-17 or IL-7.

In the second aspect of the present disclosure, a use of mesenchymal stem cells is provided for preparing a pharmaceutical composition for promoting IL-4 expression and/or activity.

In the third aspect of the present disclosure, a method is provided for screening a candidate compound for preventing or treating lymphocyte reduction and/or immunosuppression induced by stress response, said method comprising the following step:

(a) in a testing group, adding a testing compound into a cell culture system treated with stress response, and observing lymphocyte reduction; and in a control group, no testing compound being added into an identical cell culture system, and observing lymphocyte reduction;

wherein, if the lymphocyte reduction of the testing group is significantly lower than that of the control group, then the testing compound is screened out to be a candidate compound for preventing or treating lymphocyte reduction and/or immunosuppression induced by stress response.

In another preferred embodiment, cells in the cell culture system treated with stress response include (a) cells isolated from animals treated with stress response; and/or (b) cells treated with glucocorticoids in vitro.

In another preferred embodiment, said reduction comprises the lymphocyte reduction caused by apoptosis.

In another preferred embodiment, said "significantly lower than" means that the number of apoptotic lymphocytes (or the amounts of reduction) in the testing group is lower than 50% of the number of apoptotic lymphocytes (or the amount of reduction) in the control group.

In another preferred embodiment, said method further comprises the following step:

(b) detecting IL-4 expression and/or activity in the cell system of the testing group and the control group;

wherein, if IL-4 expression and/or activity in the testing group is significantly higher than that of the control group, the testing compound is screened out to be a candidate compound for preventing or treating lymphocyte reduction and/or immunosuppression induced by stress response.

In another preferred embodiment, said "significantly higher than" means that the IL-4 expression and/or activity in the testing group is at least higher than that in the control group by 50%.

In the fourth aspect of the present disclosure, a method is provided for preventing or treating lymphocyte reduction induced by stress response and/or immunosuppression induced by stress responses by administering a safe and effective amount of mesenchymal stem cells to a subject in need thereof.

In another preferred embodiment, said subject includes mammals (eg. human).

In another preferred embodiment, the application dosage of the safe and effective amount of mesenchymal stem cells is $0.01-10\times10^6$ mesenchymal stem cells/kg.

It should be understood that in the present disclosure, the technical features specifically described above and below (such as in the Examples) can be combined with each other, thereby constituting a new or preferred technical solution which needs not be described one by one.

Figure 1:
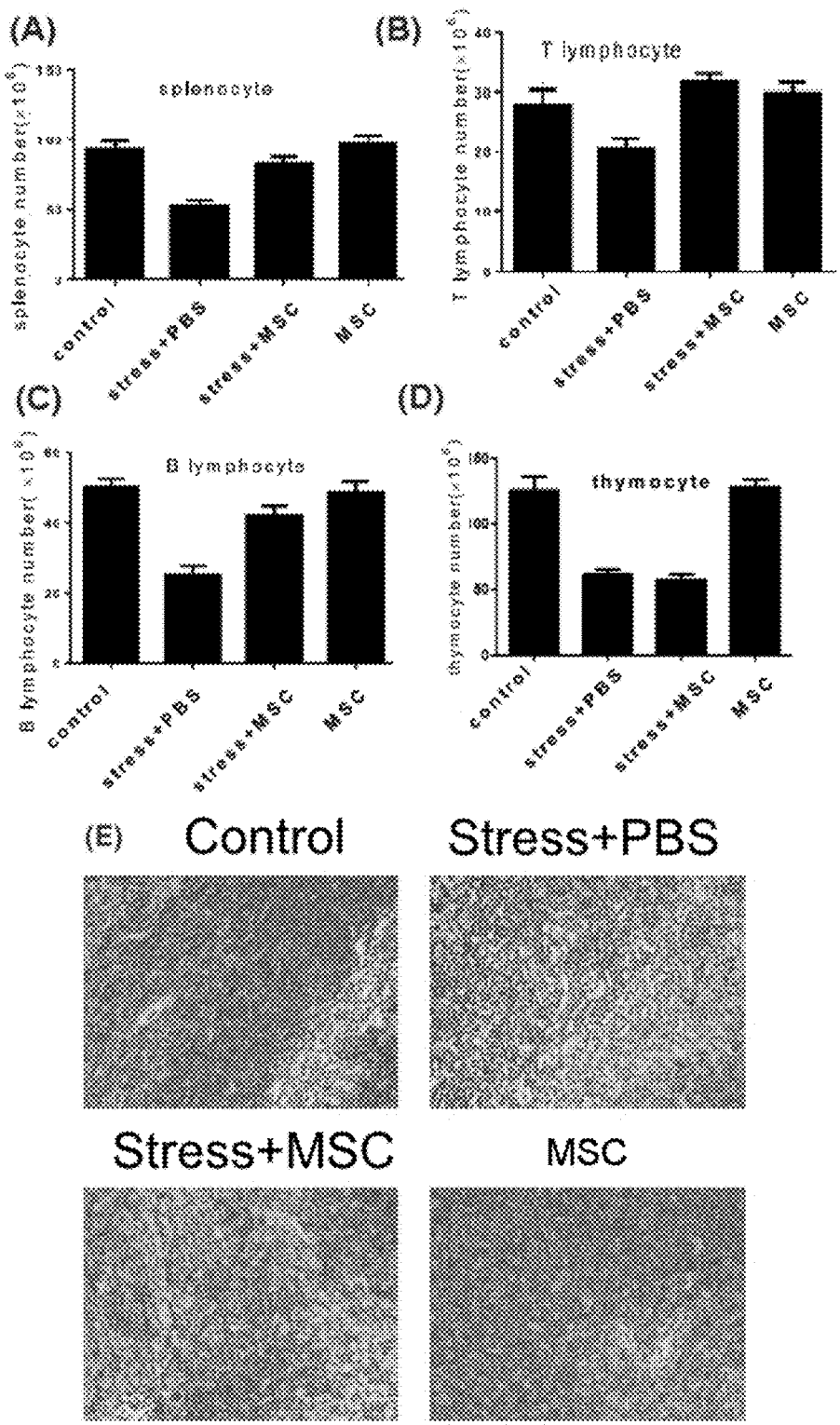
FIG. 1 shows that MSCs inhibited the lymphocyte reduction induced by restraint stress.

Male BALB/c mice (6-8 weeks old) were injected with $1\times10^6$ MSCs or PBS through caudal vein before subjected to restraint stress treatment. After two rounds of restraint stress treatment, the total numbers of splenocytes and thymocytes of the mice were counted (FIGS. 1A and B). The relative ratio of T-lymphocytes and B-lymphocytes was analyzed by flow cytometry, and the corresponding absolute amounts of T-lymphocytes and B-lymphocytes were obtained by multiplying the absolute total number of splenocytes (Figs. C and D). in vivo apoptosis of splenocytes was evaluated by TUNEL method.

Figure 2:
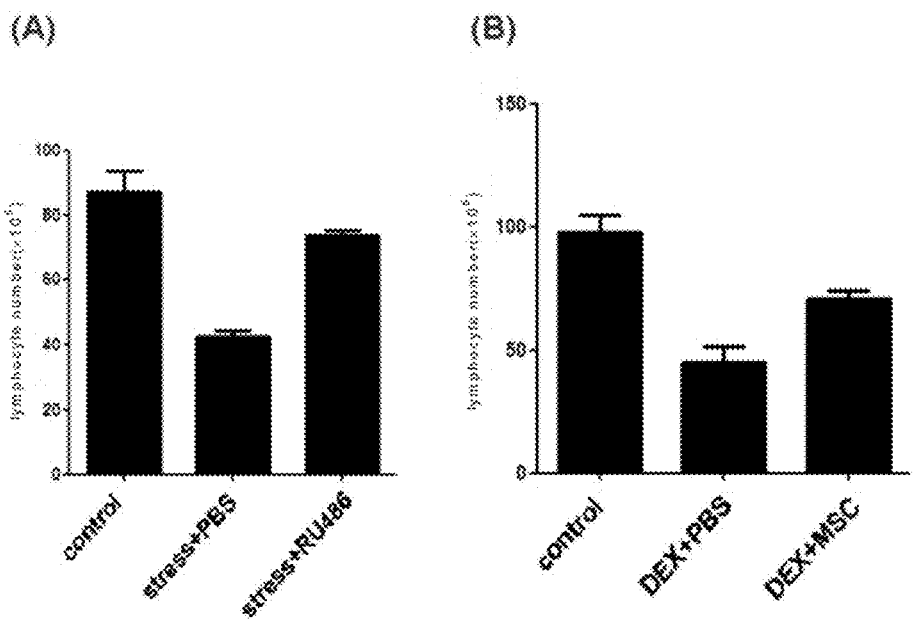

FIG. 2: the lymphocyte reduction induced by restraint stress was mediated by glucocorticoids.

Male BALB/c mice (6-8 weeks old) were injected with $1\times10^6$ MSCs, PBS, or glucocorticoid antagonist RU486 (25 mg/kg) through caudal vein before subjected to restraint stress treatment. After two rounds of restraint stress treatment, the number of lymphocytes was counted (FIG. 2A). Male BALB/c mice (6-8 weeks old) were intraperitoneally injected with dexamethasone (5 mg/kg) and $1\times10^6$ MSCs or PBS through caudal vein respectively at the same time. The splenocytes of the mince were counted after 2 days.

Figure 3:
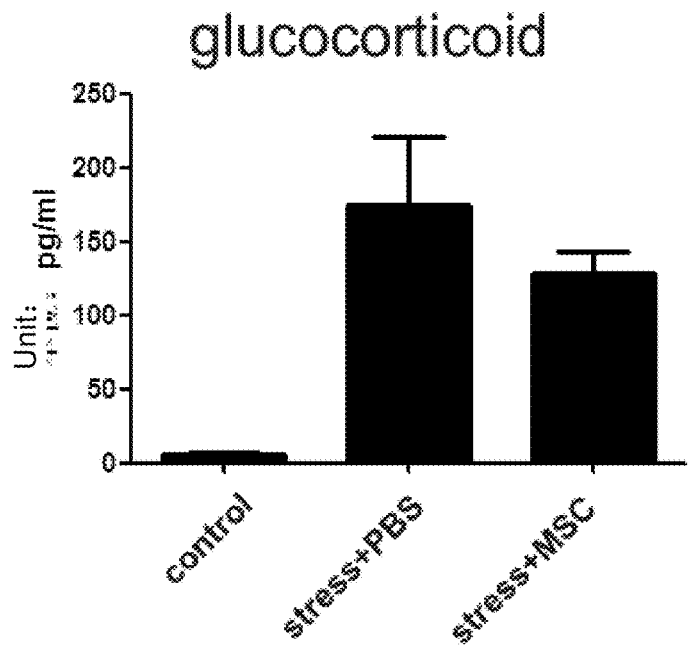

FIG. 3: MSCs did not affect restraint stress-induced glucocorticoid production

Serum was collected from the mice after 2-round restraint stress and the glucocorticoid content in the serum was determined by ELISA.

Figure 4:
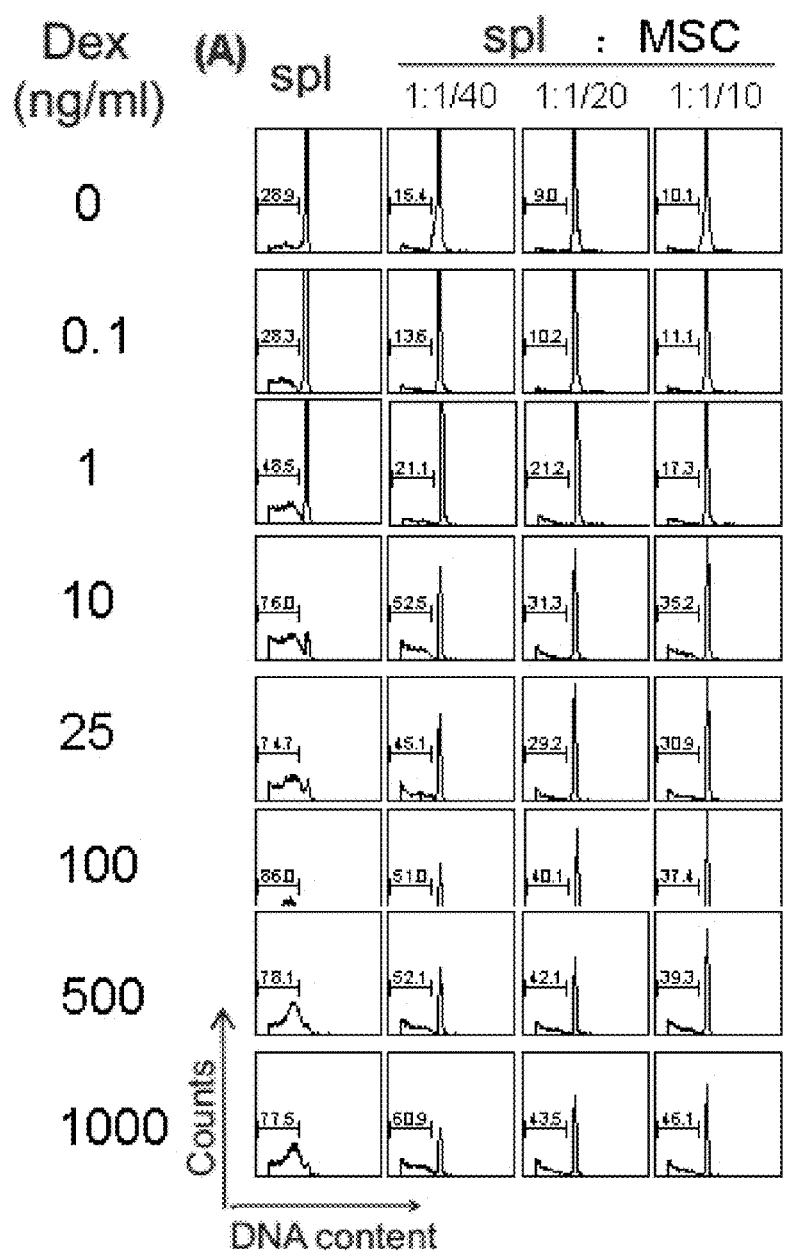
Figure 4:
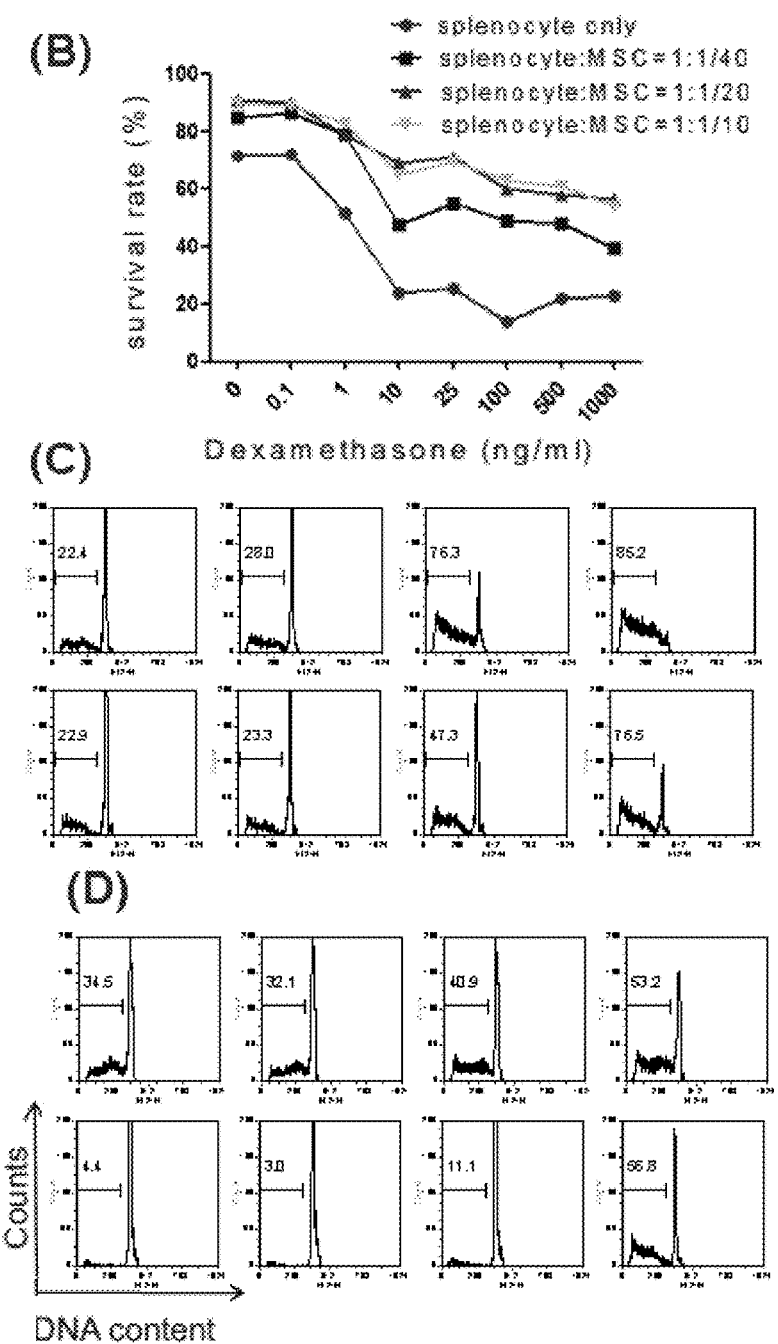

FIG. 4: MSCs protected lymphocytes from dexamethasone-induced apoptosis $2\times10^5$ splenocytes were co-cultured with different amounts of MSCs at ratios of 1:1/40, 1:1/20 and 1:1/10. Dexamethasone with different concentrations was added into the co-culture system respectively. Splenocytes were harvested 30 hours later and then stained with PI and the PI stained-splenocytes were analyzed for DNA content by flow cytometry (FIG. 4A). 100% minus the percentage of hypodiploid in Fig A to obtain the survival rate of splenocytes. The purified T-lymphocytes and B-lymphocytes were subjected to the similar analysis for splenocytes in Figure A (FIGS. 4C and 4D).

Figure 5:
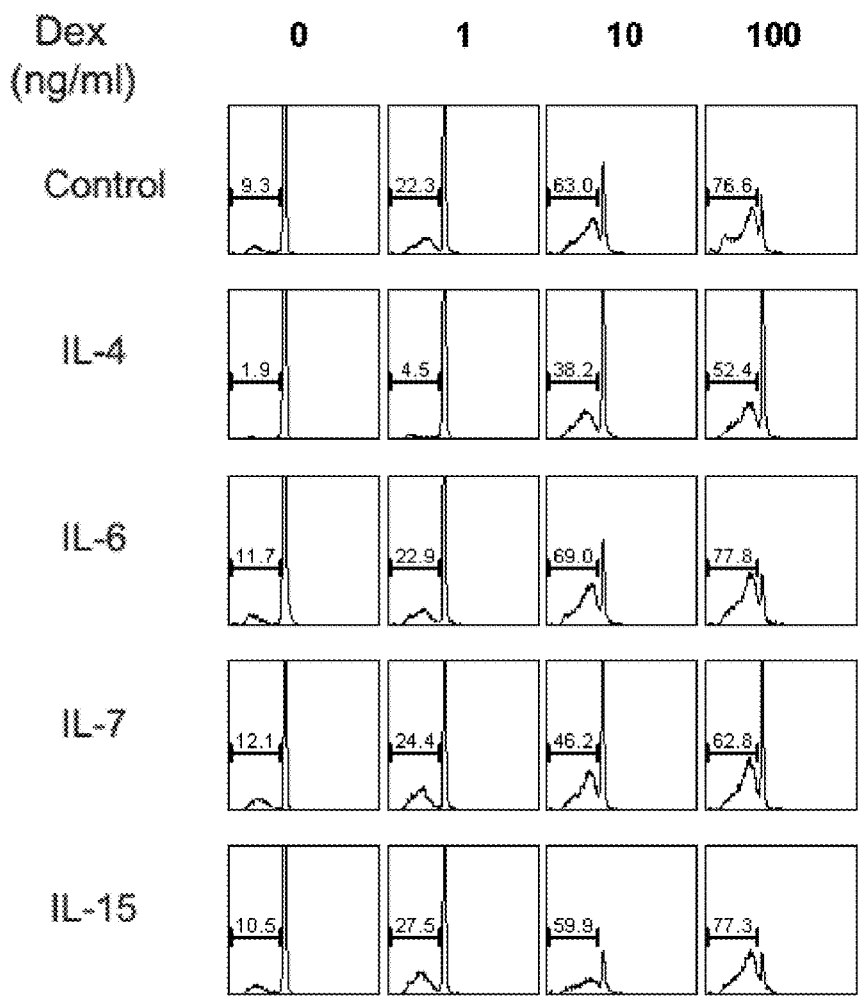

FIG. 5: Interleukin-4 significantly abrogated dexamethasone-induced lymphocyte apoptosis Splenocytes were cultured in culture media containing dexamethasone with different concentrations, and IL-4, IL-6, IL-7 or IL-15 was added respectively (10 ng/ml). After 24 hours, cells were collected and subjected to PI staining, and DNA content was analyzed by flow cytometry.

Figure 6:
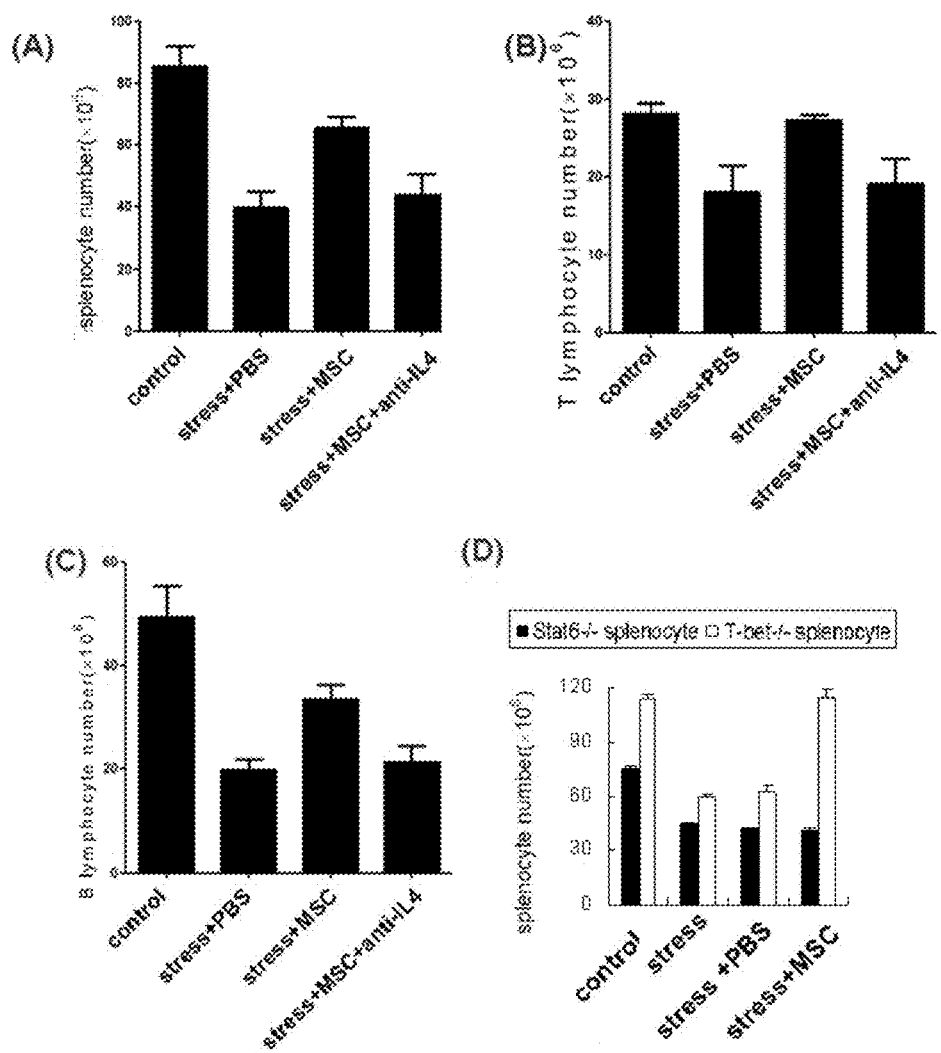

FIG. 6: the protection of MSCs on restraint stress-induced lymphocyte reduction depends on IL-4

Male BALB/c mice (6-8 weeks old) were injected with PBS, MSCs, or MSCs and neutralizing antibodies to IL-4 before subjected to the restraint stress. The numbers of T-cells and B-cells were determined (the same method as that in FIG. 1). STATE-deficient mice and T-bet-deficient mice were subjected to two rounds of restraint stress, and then, the numbers of lymphocytes were counted.

Figure 7:
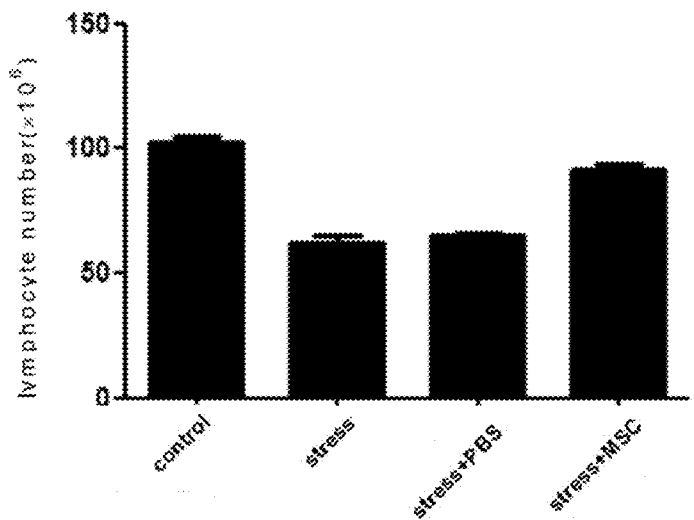

FIG. 7: the therapeutic effect of MSCs on restraint stress-induced lymphocyte reduction Male BALB/c mice (6-8 weeks old) were injected with PBS or MSCs after subjected to the restraint stress. The numbers of lymphocytes in the mice spleen were determined after two rounds of stress.

Figure 8:
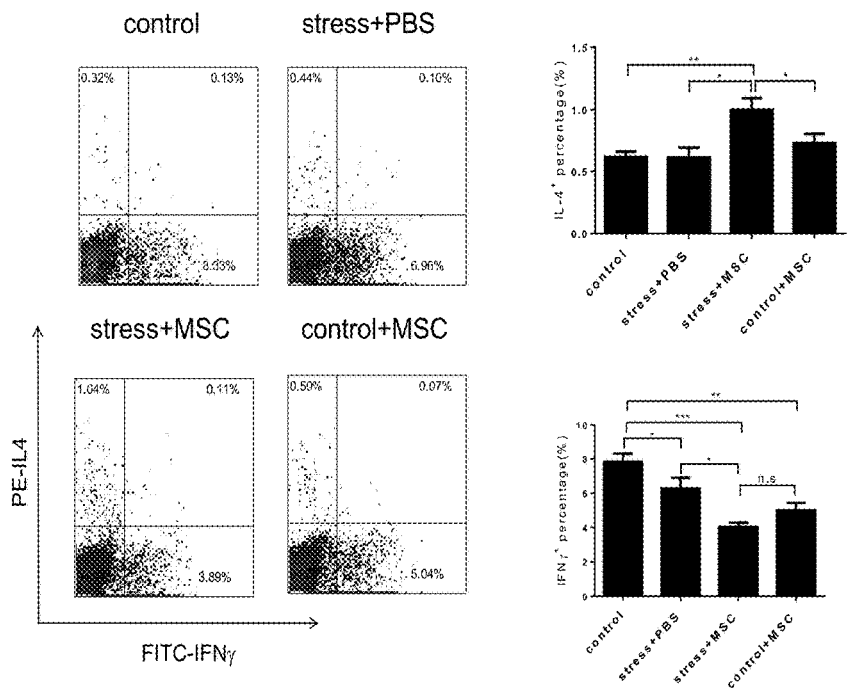

FIG. 8: compared with the normal control group, MSCs-injecting group or the restraint stress group, the mice injected with MSCs in the restraint stress group showed that the ratio of splenocytes which secrete IL-4 was significantly up-regulated.

DETAILED DESCRIPTION OF THE DISCLOSURE

Upon extensive and intensive research, the inventor surprisingly found the prophylaxis or therapeutic effects of mesenchymal stem cells on stress induced lymphocyte reduction or immunosuppression for the first time. Unlike the use of mesenchymal stem cells in inhibiting inflammatory reaction, the inventors found that mesenchymal stem cells unexpectedly prevent the dexamethasone-induced lymphocyte reduction through regulating IL-4, thereby possessing the function of activating immunoreaction. Based on the above findings, the present disclosure is accomplished.

Terms

As used herein, the term "stress response", "stress" and "pressure" can be used interchangeably and all refer to stress, which means a physiological phenomenon of rapid increase in the concentration of blood adrenocorticotrophic hormone and massive glucocorticoid production through hypothalamus induced by a sudden, strong and harmful stimuli (such as trauma, surgery, blood loss, infection, toxicity, anoxia, or hungry, etc.) to the body. Extensive neuroendocrine reactions can be induced by stress. A persistent stress or over-stress may result in the onset of a variety of physiological or psychological diseases.

Mesenchymal Stem Cells

Mesenchymal stem cells (MSCs) are pluripotent adult stem cells that can be readily isolated from various tissues, including bone marrow, fat tissue, or umbilical cord, etc. Compared with other kinds of stem cells, such as embryonic stem cells, mesenchymal stem cells have advantages in many aspects. For example, unlike embryonic stem cells, no ethical issues will be involved in clinical use for mesenchymal stem cells; or mesenchymal stem cells are not tumorigenic in vivo. Besides, mesenchymal stem cells are low immunogenic and will not be easily rejected by the acceptor. These advantages of mesenchymal stem cells enable them to be ideal candidate cells for clinical cell therapy.

Mesenchymal stem cells are closely linked with immune system. In the past few years, mesenchymal stem cells were used to treat many diseases caused by immune hyperfunction, such as multiple sclerosis, graft-versus-host immunodiseases, type I diabetes, rheumatic arthritis, systemic lupus erythematosus, and excellent therapeutic effects were obtained.

Researches demonstrated that when contacting with the inflammatory factors-interferon γ and TNF α, IL-1α or IL-1β, mesenchymal stem cells obtain the immune suppressing function by secreting nitric oxide and chemotactic factors. The combined effects of nitric oxide and chemotactic factors can significantly suppress the immune reaction.

However, according to the experiments, the inventors found that, for the pathogenesis of immunosuppression induced by stress, mesenchymal stem cells possess a function of activating immunocytes, (lymphocytes), thereby improving the immunity.

The kinds of mesenchymal stem cells which can be used in the present disclosure are not specifically limited, and may comprise mesenchymal stem cells derived form bone marrow, fat, umbilical cord, placenta, or amniotic fluid, etc.

The mesenchymal stem cells which can be used in the present disclosure are in a form of liquid and contain $0.05$-$5 \times 10^6$ cells/ml, preferably, $1$-$2 \times 10^6$ cells/ml. The amounts of the mesenchymal stem cells are $0.01$$10 \times 10^6$/kg for administration.

Interleukin-4 (IL-4)

IL-4 has a lot of biological functions, including inducing B-cells, activating T-cells, and promoting B-cells to differentiate to plasmocytes, and plays an essential role in humoral immunity and acquired immunity. IL-4 can protect or prevent lymphocytes from apoptosis. Besides, IL-4 can further promotes the antigen presentation and tumor-cell killing functions of macrophages.

The concentration of IL-4 used in the present disclosure is not specifically limited, and it can be any proper concentration for applying to cells or animals. Generally, for the cell experiments, the concentration of IL-4 is 1 ng/ml-50 ng/ml, and/or for the animal experiments, the concentration of IL-4 is 0.5 mg/kg-10 mg/kg.

In the present disclosure, IL-4 can be further used as an additional ingredient in the pharmaceutical composition for preventing or treating stress-induced lymphocyte reduction and/or immunosuppression so as to prevent or treat lymphocyte reduction and/or immunosuppression induced by the increased glucocorticoids.

Pharmaceutical Composition

A pharmaceutical composition for preventing or treating stress-induced lymphocyte reduction and/or immunosuppression prepared by using mesenchymal stem cells is provided in the present disclosure. Wherein, the pharmaceutical composition contains a safe and effective amount of mesenchymal stem cells and pharmaceutically acceptable carriers.

When therapeutically applying (administering) the composition, IL-4 expression and/or activity can be increased to inhibit lymphocyte reduction and/or immunosuppression due to the increased glucocorticoids in the body during the stress reaction. Generally, the mesenchymal stem cells can be prepared in a medium of non-toxic, inert and pharmaceutically acceptable aqueous carriers, wherein, pH is generally about 58, preferably about 6-8 although pH value can be varied with the characters of prepared substances and the diseases to be treated. The prepared pharmaceutical composition can be administered through conventional routes comprising (but not limited to): intramuscular, intravenous, subcutaneous, intracutaneous, or topical administration.

The pharmaceutical composition of the present disclosure comprises a safe and effective amount of mesenchymal stem cells, a pharmaceutically acceptable carrier(s) or excipient(s) and optional IL-4. These carriers include (but are not limited to): saline, buffer solution, glucose, water, glycerol, ethanol, or combinations thereof. The pharmaceutical preparation should match the administration mode. The pharmaceutical composition of the present disclosure can be prepared into a form of injection, such as with saline or aqueous solution containing glucose or other auxiliaries by conventional methods. Pharmaceutical compositions, such as tablets and capsules, can be prepared with conventional methods. Pharmaceutical compositions such as injections, solution, tablets and capsules may be preferably produced in sterile conditions. The administration amount of the active ingredients is a therapeutically effective amount, for example, about 1 μg/kg (body weight)-10 mg/kg (body weight) per day.

Screening Method

A method for screening candidate compounds for preventing or treating stress-induced lymphocyte reduction and/or immunosuppression is also provided in the present disclosure. Wherein, the method includes screening out a compound which may affect the stress-induced lymphocyte reduction and/or immunosuppression and then determining the effects of the screened compound on lymphocytes apoptosis and IL-4 expression and/or activity.

The specific steps are:

(a) in a testing group, adding a testing compound into a cell culture system treated with stress response, and observing lymphocyte reduction; and in a control group, no testing compound being added into an identical cell culture system, and observing lymphocyte reduction;

wherein, if the lymphocyte reduction of the testing group is significantly lower than that of the control group, then the testing compound is screened out to be a candidate compound for preventing or treating lymphocyte reduction and/or immunosuppression induced by stress response.

In the present disclosure, cells in the cell culture system treated with stress response include (a) cells isolated from animals treated with stress response; and/or (b) cells treated with glucocorticoids in vitro. Said reduction comprises the lymphocyte reduction caused by apoptosis.

In another preferred embodiment, said "significantly lower than" means that the number of apoptotic lymphocytes (or amount of reduction) in the testing group is lower than 50% of the number of apoptotic lymphocytes (or amount of reduction) in the control group.

Besides, said method further comprises the following step:

(b) detecting IL-4 expression and/or activity in the cell system of the testing group and the control group;

wherein, if IL-4 expression and/or activity in the testing group is significantly higher than that of the control group, the testing compound is screened out to be a candidate compound for preventing or treating lymphocyte reduction and/or immunosuppression induced by stress response.

In another preferred embodiment, said "significantly higher than" means that the IL-4 expression and/or activity in the testing group is at least higher than that in the control group by 50%.

Materials and General Methods

1. Mice

Male BALB/c mice (8-10 weeks old) were purchased from Shanghai SLAC Inc., STAT6-deficienct (deficiency in CD4 TH2 cell development) and T-bet-deficient (deficiency in CD4 TH1 cell development) mice are purchased from Jackson Laboratory (U.S.A). All the mice were housed in the animal facility of School of Medicine, Shanghai Jiao Tong University.

2. Reagents

Recombinant interleukin-4, interleukin-6, interleukin-7 and interleukin 15 were purchased from ebioscience Co. (U.S.A). Antibody against interleukin-4 was from Harlan Co. (USA). Dexamethasone and RU486 were purchased from Sigma-Aldrich Co. (U.S.A).

3. Cells

Mesenchymal stem cells were isolated and obtained from the bone marrow of 6-8-week-old BALB/c mice. Mesenchymal stem cells were cultured in DMEM low-glucose medium supplemented with 10% fetal bovine serum, 2 mmol/L glutamine, 100 ug/ml penicillin and 100 ug/ml streptomycin.

4. Animal Model: Restraint Stress

Male BALB/c mice (8-10 weeks old) were placed in 50 ml centrifuge tube with multiple punctures for ventilation. The mice were held in the tube for 12 hours and liberated from restraint for a 12-hour rest. Food and water was provided during the rest period. Control mice were provided with food and water only during the rest period of the testing group without restraint stress treatment. After treated with restraint stress for two consecutive days, the mice were sacrificed by spinal dislocation and the spleens of the mice were collected for counts and analysis.

5. Injection of Dexamethasone and Glucocorticoid Antagonist RU486

The mice were intraperitoneally injected with dexamethasone (5 mg/kg). The spleens of the mice were collected after two days for counts and analysis. Glucocorticoid antagonist RU486 were intraperitoneally injected to the mice right before the stress started. When the stress treatment was finished, the spleens of the mice were immediately collected for counts and analysis.

6. Determining the content of glucocorticoid in the serum by ELISA

The kit was purchased from ELAab Science CO, Wuhan (Reagent Cat. No. E0540M). The assay was conducted according to the instructed procedures in the specification.

7. TUNEL Staining

The kit was purchased from ROCHE CO. (Reagent Cat. No. 11684817910). The staining was conducted according to the instructed procedures in the specification.

8. DNA Content Analysis

Cells were resuspended in PBS upon collection, subjected to centrifugation at 300 g for removing PBS, and then resuspended in PI stained aqueous solution (containing 0.1 sodium pyruvate, 0.1% Trixton-X-100 and 50 mg/L propidium iodide). The resuspended cells were maintained in the fridge at 4° C. overnight, and finally, the DNA content was determined by flow cytometry.

9. Flow Cytometry

FITC-marked CD3 antibodies and APC-marked CD19 antibodies were used to determine T-lymphocytes and B-lymphocytes respectively. The cells were incubated with FITC-CD3 and APC-CD19 antibodies at 4° C. in darkness for 30 minutes, then washed by 0.1% BSA-contained PBS twice, and finally, resuspended in 0.1% BSA-contained PBS for flow cytometry.

The Advantage Effects of the Present Disclosure

1. MSCs possess preventive and therapeutic effects on stress-induced immunosuppression to some extent.

2. MSCs prevent and treat stress-induced immunosuppression by affecting lymphocyte reduction caused by increased glucocorticoids after stress.

3. IL-4 has a protective effect on glucocorticoids-induced lymphocyte reduction during the stress response and MSCs improve the pathologic condition of the stress response by affecting IL-4.

The disclosure is further illustrated by the following examples. These examples are only intended to illustrate the disclosure, but not to limit the scope of the disclosure. For the experimental methods in the following examples the specific conditions of which are not specifically indicated, they are performed under routine conditions, e.g., those described by Sambrook. et al., in Molecular Cloning: A Laboratory Manual, New York: Cold Spring Harbor Laboratory Press, 1989, or as instructed by the manufacturers. Unless otherwise specified, the percentage and portion refer to weight percentage and weight portion.

Example 1 MSCs Prevents Lymphocyte Reduction Induced by Restraint Stress

Methods: According to general methods 3-5, 6-8 week-old male BALB/c mice were pre-injected with $1 \times 10^6$ MSCs or PBS as control through caudal vein and then immediately subjected to restraint stress. Upon two round of restraint stress, the total splenocytes of the mice were counted.

The relative ratio of T-lymphocytes and B-lymphocytes in the mice splenocytes were determined by flow cytometry and the absolute numbers of T-lymphocytes and B-lymphocytes in the splenocytes were further calculated.

Results: As shown in FIGS. 1A, B and C, restraint stress resulted in dramatic reductions of splenocytes numbers in the mice, and accordingly, significant reductions in the numbers of T-lymphocyte and B-lymphocyte can be both observed.

The number of splenocytes in the mice which were pre-injected with MSCs were not reduced significantly, and accordingly, no obvious reduction in the numbers of T-lymphocyte and B-lymphocyte was observed.

Conclusion: the results demonstrated that MSCs can prevent lymphocyte reduction induced by restraint stress. The results of TUNEL staining further showed that the restraint stress resulted in splenocytes apoptosis and pre-injection of MSCs may prevent apoptosis induced by restraint stress. This result further indicated that MSCs prevented lymphocyte reduction induced by restraint stress partially due to the splenocytes apoptosis reduction.

Example 2: Glucocorticoids are Involved in the Mediation of Lymphocyte Reduction Induced by Restraint Stress Methods: According to general method 5, 6-8 week-old male BALB/c mice were injected intraperitoneally with glucocorticoids antagonist RU486 (25 mg/kg) or PBS as control. Then the mice were subjected to restraint stress immediately. Upon two rounds of restraint stress, the total splenocytes of the mice were counted.

Results: As shown in FIG. 2A, the lymphocyte reduction induced by restraint stress was significantly improved by using glucocorticoids antagonist RU486.

Conclusion: The effects of glucocorticoids on restraint stress can be inhibited by the antagonist. Therefore, glucocorticoids are involved in the mediation of lymphocyte reduction induced by restraint stress.

Example 3 MSCs Alleviate the Lymphocyte Reduction Directly Induced by Glucocorticoids Method: According to general method 5, the mice were directly injected with dexamethasone (artificial synthetic glucocorticoids), while MSCs were injected through the caudal vein of the mice. After 36 hours, splenocytes of the mice were counted.

Results: As shown in FIG. 2B, the lymphocyte reduction induced by restraint stress was also significantly improved by using MSCs.

Conclusion: MSCs also alleviated the lymphocyte reduction directly induced by glucocorticoids.

Example 4: MSCs do not Affect the Glucocorticoid Production Induced by Restraint Stress Methods: According to general method 4, after two rounds of restraint stress to the 6-8 week-old male BABL/c mice, serum was collected from the mice and the glucocorticoid content in the serum was determined by ELISA.

Result: As shown in FIG. 3, high level of glucocorticoids in the mice could be induced by restraint stress; however, MSCs injection could hardly affect the glucocorticoid level.

Conclusion: The results demonstrated that MSCs do not affect the glucocorticoid production resulted from stress.

Example 5: MSCs Protect Lymphocytes from Apoptosis Induced by Dexamethasone In Vitro 1

Methods: $2\times10^5$ cells/ml of splenocytes were mixed and co-cultured with $5\times10^3$, $1\times10^4$, or $2\times10^4$ (unit: cells/ml) MSCs at ratio of 1:1/40, 1:1/20, or 1:1/10, respectively. Dexamethasone at concentration of 0 ng/ml, 0.1 ng/ml, 1 ng/ml, 10 ng/ml, 25 ng/ml, 100 ng/ml, 500 ng/ml, or 1000 ng/ml was respectively added into the co-culture system.

The splenocytes and MSCs were co-cultured for 30 hours, and then non-adherent splenocytes were collected for PI staining and then subjected to determination of splenocyte DNA content by flow cytometry. The cells with DNA content lower than normal diploid were considered as apoptotic cells.

Result: As shown in FIGS. 4A and 4B, the ratio of the cells with content lower than normal diploid, that is, the apoptotic cells ratio, gradually grows with the increased dexamethasone concentration. Meanwhile, MSCs significantly diminished splenocyte apoptosis induced by dexamethasone at the number of 1/40 of the splenocytes. When the number of MSCs was increased to 1/20 of the splenocytes, MSCs further diminished the cell apoptosis level induced by dexamethasone. When the number of MSCs was increased to 1/10 of splenocytes, MSCs did not further diminish the cell apoptosis level induced by dexamethasone.

Conclusion: In a certain range, MSCs protects splenocytes from apoptosis induced by dexamethasone in a dose-dependent manner. Wherein, when the number of MSCs is 1/20 of splenocytes, the protective effect on splenocytes apoptosis induced by dexamethasone approaches the maximum.

Example 6 MSCs Protect Lymphocytes from Apoptosis Induced by Dexamethasone In Vitro 2

Methods: the method was similar to Example 5 except that $2\times10^5$ cells/ml of purified T-lymphocytes and $2\times10^5$ cells/ml of B-lymphocytes were co-cultured with $1\times10^4$ cells/ml MSC and dexamethasone at concentration of 0.1 ng/ml, 1 ng/ml, or 10 ng/ml was added into the co-cultured system. DNA contents of T-lymphocytes and B-lymphocytes were detected after 30 hours to determine the apoptosis condition of T-lymphocytes and B-lymphocytes.

Results: As shown in FIG. 4C, for T-lymphocytes, MSCs significantly protected T-lymphocytes from apoptosis when the dexamethasone concentration is 1 ng/ml; and MSCs protected T-lymphocytes from apoptosis when the dexamethasone concentration is 0.1 ng/ml and 10 ng/ml.

As shown in FIG. 4D, for B-lymphocytes, MSCs significantly protected B-lymphocytes from apoptosis when the dexamethasone concentrations are 0.1 ng/ml and 1 ng/ml; and MSCs hardly protected B-lymphocytes from apoptosis when the dexamethasone concentration is 10 ng/ml.

Conclusion: the test result demonstrated that MSCs protect T-lymphocytes from apoptosis induced by dexamethasone at moderate doses to some extent and significantly protect B-lymphocytes from apoptosis induced by dexamethasone at low doses.

Example 7: IL-4 Effectively Protect Lymphocytes from Apoptosis Induced by Dexamethasone Method: Splenocytes were treated with dexamethasone with different concentrations (0, 1, 10, 100 ng/ml) and different cytokines, IL-4, IL-6, IL-7 or IL-15 (the concentration is 10 ng/ml), were added into the culture system. DNA content of the splenocytes were detected after 24 hours to determine the apoptosis condition of the splenocytes.

Results: As shown in FIG. 5, the numbers in the figure represent the ratio of hypodiploids, that is, the apoptosis level. The hypodiploid content in the splenocytes was increased by dexamethasone with a dose-dependent manner and was abrogated by IL-4 the most effectively. Other cytokines IL6, IL-7 or IL-15 failed to abrogate the hypodiploid content in the splenocytes increased by dexamethasone.

Conclusion: Compared with other interleukins, IL-4 can most effectively protect lymphocytes from apoptosis induced by dexamethasone.

Example 8: MSCs Protect Lymphocytes from Reduction Induced by Restraint Stress Through IL-4

Method: The 6-8 week-old BALB/c mice were intraperitoneally pre-injected with MSCs through caudal vein and neutralizing antibodies to IL-4. Other three groups of mice were injected with MSCs or PBS or blank as control. The mice were subjected to two rounds of restraint stress immediately. After the treatment was ended, the total number of splenocytes was counted. The relative ratios of T-lymphocytes and B-lymphocytes in the mice splenocytes were determined by flow cytometry and the absolute amounts of T-lymphocytes and B-lymphocytes in the splenocytes were further calculated.

Result: As shown in FIGS. 6A-C, MSCs can effectively protect lymphocytes from reduction induced by restraint stress; however, when IL-4 was neutralized by the antibodies, MSCs failed to protect lymphocytes from reduction induced by restraint stress.

Conclusion: The testing result shows that the injection of neutralizing antibodies to IL-4 can alleviate the protection from MSCs to the lymphocyte reduction induced by restraint stress. Therefore, the protective effect of MSCs is dependent on IL-4.

Example 9: The Effects of MSCs on Lymphocyte Reduction in the IL-4 Signal Transduction-Deficient Model Method: STAT6-deficient mice (IL-4 signal transduction-deficient) were used as testing group 1 for restraint stress and were injected with MSCs. The numbers of mononuclear cells, T-lymphocytes and B-lymphocytes in splenocytes were analyzed. The method for testing group 2 was similar to that of testing group 1 was used. T-bet-deficient mice were used as the animal model. STAT6 deficient mice or T-bet-deficient mice without stress treatment were used as control group.

Results: As shown in FIG. 6D, the lymphocyte reduction in STAT6-deficient mice was significantly induced by restraint stress; however, the lymphocyte reduction in STAT6-deficient mice induced by restraint stress could not be inhibited by MSCs while MSCs could protect T-bet-deficient mice from lymphocyte reduction induced by restraint stress.

Conclusion: The test result shows that MSCs fail to protect STAT6-deficient mice which are deficient in IL-4 signal transduction from lymphocyte reduction induced by restraint stress, which further demonstrates that the protective effect of MSCs is dependent on IL-4.

Example 10: MSCs Promote the Secretion of IL-4 by Splenocytes

Method: The 6-8 week-old BALB/c mice were pre-injected with $1 \times 10^6$ MSCs or PBS as control through caudal vein and then immediately subjected to restraint stress. After two rounds of restraint stress, the expression levels of IL-4 and interferon-γ in the splenocytes were determined by flow cytometry.

Result: As shown in FIG. 8, compared with the normal control group, the MSCs injection group and the restraint stress group, the mice in the restraint stress group accepting MSCs injection showed an obvious up-regulation of IL-4-secreting splenocyte ratio. Compared with the control group and the restraint stress group, the restraint stress group accepting MSCs injection showed a down-regulation of IFN-γ-secreting splenocytes, however, there is no significant difference when compared with the group accepting MSCs injection alone.

Conclusion: IL-4 secretion can be up-regulated in the restraint stressed mice which accept MSCs injection.

Experiment 11

MSCs Treat Lymphocyte Reduction Induced by Restraint Stress

Method: According to general methods 3-5, the 68 week-old male mice were subjected to two rounds of restraint stress. After the first round of stress, $1 \times 10^6$ of MSCs or PBS (as control) were injected through caudal vein; and after the second round of stress, the lymphocytes in the mice spleen were counted.

Result: As shown in FIG. 7, the numbers of lymphocytes were significantly reduced by restraint stress. However, the number of lymphocytes in the mice spleen of the MSCs treatment group was hardly reduced.

Conclusion: MSCs can effectively treat lymphocyte reduction induced by restraint stress.

Discussion

For years, MSCs have been considered to be important in immune system disorders with immune hyperfunction as the major mechanism. However, the inventors found that MSCs become immuno-promoting in the microenvironment with weak immune response. The "buffer ability" of the MSCs for maintaining the immune response at a certain level may be a foundation for studying the function of MSCs for affecting the influence of stress on immune system so as to achieve the goal of alleviating the negative influence of stress on disease development and progression.

All references mentioned in the present disclosure are incorporated herein by reference, as each of them is individually cited herein by reference. Further, it should be understood that, after reading the above contents, the skilled person can make various modifications or changes to the present disclosure. All these equivalents also fall into the scope defined by the appending claims of the present application.

The invention claimed is:

1. A method for preventing or treating stress response-induced lymphocyte reduction and/or stress response-induced immunosuppression, wherein said method comprises:
    administering a pharmaceutical composition comprising a safe and effective amount of mesenchymal stem cells to a subject in need thereof, wherein the stress response-induced immunosuppression includes T-lymphocyte reduction induced by apoptosis, and wherein said mesenchymal stem cells are selected from the group consisting of umbilical cord mesenchymal stem cells, adipose mesenchymal stem cells, and bone marrow mesenchymal stem cells.

2. The method according to claim 1, wherein said stress response-induced lymphocyte reduction comprises lymphocyte reduction induced by increased glucocorticoids.

3. The method according to claim 1, wherein the mesenchymal stem cells are derived from a mammal.

4. The method according to claim 1, wherein said stress induced-immunosuppression includes decrease in the expression and/or activity of Interleukin-4 (IL-4).

5. The method according to claim 1, wherein said mesenchymal stem cells are derived from a human, a mouse, or a rat.

6. The method according to claim 1, wherein said pharmaceutical composition comprises mesenchymal stem cells and a pharmaceutically acceptable carrier.

7. The method according to claim 1, wherein said pharmaceutical composition further comprises additional active ingredient IL-4.

8. The method according to claim 1, wherein said pharmaceutical composition is in a liquid form and comprises $0.05\text{-}10 \times 10^6$ cells/ml.

9. The method according to claim 1, wherein the effective amount of said mesenchymal stem cells is $0.01\text{-}100 \times 10^6$ mesenchymal stem cells/kg.

* * * * *